US007332348B2

(12) United States Patent
Sandell

(10) Patent No.: US 7,332,348 B2
(45) Date of Patent: Feb. 19, 2008

(54) SAMPLE SUBSTRATE HAVING A DIVIDED SAMPLE CHAMBER AND METHOD OF LOADING THEREOF

(75) Inventor: Donald R. Sandell, San Jose, CA (US)

(73) Assignee: Applera Corporation, Foster City, CA (US)

( * ) Notice: Subject to any disclaimer, the term of this patent is extended or adjusted under 35 U.S.C. 154(b) by 688 days.

(21) Appl. No.: 10/378,580

(22) Filed: Feb. 28, 2003

(65) Prior Publication Data

US 2004/0171170 A1 Sep. 2, 2004

(51) Int. Cl.
*G01N 1/10* (2006.01)
*A61M 37/00* (2006.01)
*A61F 13/00* (2006.01)

(52) U.S. Cl. ......................... 436/180; 604/87; 604/306

(58) Field of Classification Search ................ 436/180; 604/87, 306

See application file for complete search history.

(56) References Cited

U.S. PATENT DOCUMENTS 4,593,819 A 6/1986 Will
4,693,711 A * 9/1987 Bremer et al. .............. 604/306
4,721,679 A 1/1988 Yiu et al.
4,965,047 A * 10/1990 Hammond ................... 422/58
5,038,852 A 8/1991 Johnson et al.
5,147,337 A * 9/1992 Plone ......................... 604/306
5,234,974 A * 8/1993 Calhoun et al. ............ 523/169
5,333,675 A 8/1994 Mullis et al.
5,342,581 A 8/1994 Sanadi
5,346,672 A 9/1994 Stapleton et al.
5,443,890 A 8/1995 Öhman
5,475,610 A 12/1995 Atwood et al.
5,484,734 A 1/1996 Kimura
5,487,782 A 1/1996 Hafeman et al.
5,593,130 A 1/1997 Hannson et al.
5,632,399 A 5/1997 Palmieri et al.
5,656,493 A 8/1997 Mullis et al.
5,683,659 A 11/1997 Hovatter
5,722,553 A 3/1998 Hovatter
5,749,730 A 5/1998 Johnsen et al.
5,863,791 A 1/1999 Baldszun et al.
5,928,907 A 7/1999 Woudenberg et al.
6,000,535 A 12/1999 Berk et al.
6,005,183 A 12/1999 Akai et al.
6,015,674 A 1/2000 Woudenberg et al.
6,027,694 A 2/2000 Boulton et al.
6,042,789 A 3/2000 Antonenko et al.

(Continued)

FOREIGN PATENT DOCUMENTS

DE 101 33 013 A1 7/2001

(Continued)

OTHER PUBLICATIONS

Partial International Search for Application No. PCT/US2004/005846 mailed Jul. 19, 2004.

(Continued)

*Primary Examiner*—Jill Warden
*Assistant Examiner*—Lore Ramillano

(57) ABSTRACT

A sample substrate configured for samples of biological material is provided. The sample substrate has a dual chambered sample well separated by a wall that may be punctured or otherwise breached to allow mixing of material contained in the two initially separate chambers. The chambers are connected by channels to fluid reservoirs, wherein the channels can be staked to prevent further fluid flow into and out of the chambers. Methods of loading a sample substrate are also provided.

6 Claims, 8 Drawing Sheets

U.S. PATENT DOCUMENTS

| | | | | |
|---|---|---|---|---|
| 6,161,696 | A | 12/2000 | Lashley | |
| 6,193,088 | B1 | 2/2001 | Vincent et al. | |
| 6,229,603 | B1 | 5/2001 | Coassin et al. | |
| 6,340,589 | B1 | 1/2002 | Turner et al. | |
| 6,383,820 | B1 | 5/2002 | Bunn et al. | |
| 6,436,350 | B1 | 8/2002 | Stanchfield et al. | |
| 6,814,935 | B2 * | 11/2004 | Harms et al. | 422/99 |
| 2002/0028507 | A1 | 3/2002 | Heimberg et al. | |
| 2002/0092767 | A1 | 7/2002 | Bjornson et al. | |
| 2002/0173745 | A1 | 11/2002 | Santini, Jr. et al. | |
| 2002/0187560 | A1 | 12/2002 | Pezzuto et al. | |

FOREIGN PATENT DOCUMENTS

| | | | |
|---|---|---|---|
| EP | 0 279 574 | A1 | 8/1988 |
| EP | 0 606 534 | A1 | 7/1994 |
| EP | 0 754 496 | A1 | 1/1997 |
| EP | 0 873 789 | A2 | 4/1998 |
| WO | WO 86/07288 | A1 | 12/1986 |
| WO | WO 01/15807 | A1 | 3/2001 |
| WO | WO 02/00347 | A2 | 1/2002 |
| WO | WO 02/01180 | A2 | 1/2002 |
| WO | WO 02/01181 | A2 | 1/2002 |

OTHER PUBLICATIONS

PCT International Search Report for International Application No. PCT/US2004/005846, mailed Nov. 10, 2004.

* cited by examiner

SAMPLE SUBSTRATE HAVING A DIVIDED SAMPLE CHAMBER AND METHOD OF LOADING THEREOF

FIELD

The present teachings relate generally to a sample substrate configured for samples of biological material, and methods of loading a sample substrate. The present teachings further relate, in various aspects, to various sample substrates having a dual chambered sample chamber separated by a wall that may be punctured or otherwise breached to allow mixing of material contained in the two initially separate chambers.

BACKGROUND

Biological testing has become an important tool in detecting and monitoring diseases. In the biological testing field, thermal cycling is used to amplify nucleic acids by, for example, performing polymerase chain reactions (PCR) and other reactions. PCR, for example, has become a valuable research tool with applications such as cloning, analysis of genetic expression, DNA sequencing, and drug discovery. Methods such as PCR may be used to detect a reaction of a test sample to an analyte-specific fluid. Typically, an analyte-specific fluid is placed in each sample chamber in advance of performing the testing. The test sample is then later inserted into the sample chambers, and the sample well tray or microcard is then transported to a thermal cycling device.

Recent developments in the field have led to an increased demand for biological testing devices. Biological testing devices are now being used in an increasing number of ways. It is desirable to provide a more efficient and compact method and structure for filling and thermally cycling substrates such as sample trays and microcards.

In typical systems, the sample tray or microcard is loaded with fluid, then loaded with the test sample, and then transported and inserted into a separate device for thermal cycling. It is desirable to reduce the amount of time and number of steps taken to fill and thermally cycle a sample tray or microcard.

SUMMARY

In accordance with the present teachings, a sample substrate for biological samples is provided comprising a first chamber portion configured to contain a biological sample at least partially defined by a first member, a second chamber portion configured to contain a biological sample at least partially defined by a second member, and a wall positioned between the first and second chamber portions. The wall in one position prevents fluid communication between the first and second chamber portions, and in another position is breached to permit fluid communication between the first and second chamber portions.

According another aspect of the present teachings, a sample substrate for biological samples is provided comprising a sample chamber where portions of the sample chamber are defined by a first member, a second member, and a wall. In one position the sample chamber is configured to hold a first fluid from a first channel, and in a second position the sample chamber is configured to be larger than the sample chamber in the first position and to additionally hold a second fluid from a second channel.

According to yet another aspect of the present teachings, a microcard is provided comprising a first network of channels in fluid communication with a plurality of chambers, and a second network of channels in fluid communication with the plurality of chambers. The first and second networks are positioned in a first and second substantially parallel planes respectively, where each of the plurality of chambers connects the first network in a first direction towards the first plane, and each of the plurality of chambers connects with the second network in a second direction toward the second plane.

In another aspect, a method of filling a sample substrate with a biological sample is provided. The method comprises filling at least a portion of a sample chamber with a first fluid through a first channel, filling at least a portion of a sample chamber with a second fluid through a second channel, and triggering at least one of the sample chamber portions so that the first and second fluids are in fluid communication with each other.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate several exemplary embodiments. In the drawings.

DESCRIPTION OF VARIOUS EMBODIMENTS

Figure 1:
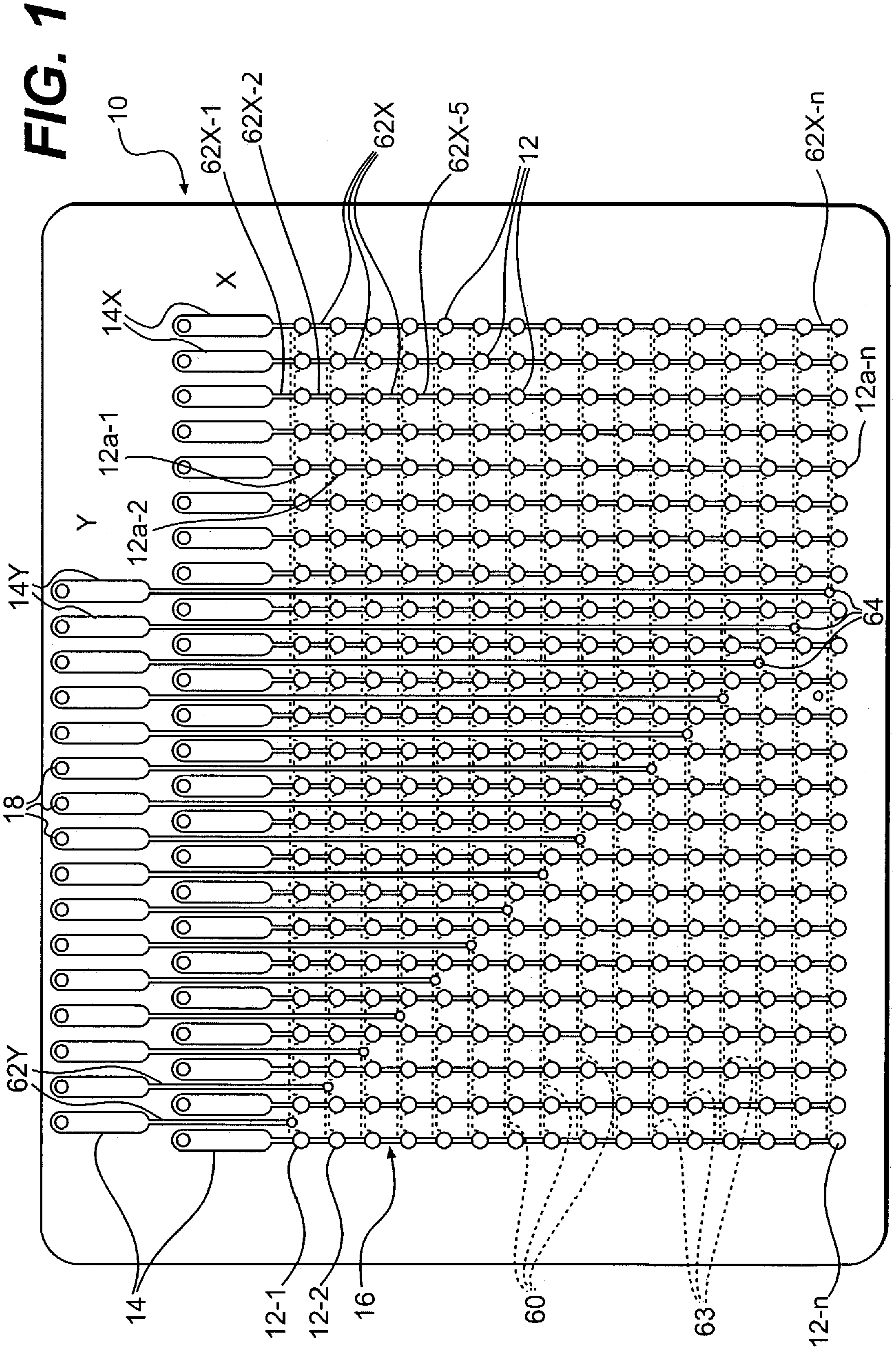
FIG. 1 is a plan view of a microcard according to one exemplary embodiment.

Reference will now be made to various exemplary embodiments, examples of which are illustrated in the accompanying drawings. Wherever possible, the same reference numbers are used in the drawings and the description to refer to the same or like parts.

In accordance with various embodiments, a sample substrate is provided having a plurality of sample chambers. In one aspect, the sample substrate comprises a plurality of sample chambers, each in fluid communication with a reservoir via a fill channel. It should be understood that although the term "microcard" is used in the specification, the present teachings are suitable in any type of sample substrate such as, for example, micro-titer plates, sample trays, etc.

Although terms like “horizontal,” “vertical,” “top,” “bottom,” “convex,” “concave,” “inside,” and “outside” are used in describing various aspects of the present teachings, it should be understood that such terms are for purposes of more easily describing the present teachings, and do not limit the scope of the teachings.

In various embodiments, such as that depicted in FIG. 1, a sample substrate such as a microcard 10 is provided. Microcard 10 may be configured for thermally cycling samples of biological material in a thermal cycling device. The thermal cycling device may be configured to perform nucleic acid amplification on samples of biological material. One common method of performing nucleic acid amplification of biological samples is polymerase chain reaction (PCR). Various PCR methods are known in the art, as described in, for example, U.S. Pat. Nos. 5,928,907 and 6,015,674 to Woudenberg et al., commonly assigned, the complete disclosures of which are hereby incorporated by reference for any purpose. Other methods of nucleic acid amplification include, for example, ligase chain reaction, oligonucleotide ligations assay, and hybridization assay.

In various embodiments, the microcard may be used in a thermal cycling device that performs real-time detection of the nucleic acid amplification of the samples in the sample chamber tape section during thermal cycling. Real-time detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling in a manner known in the art. Real-time detection permits more accurate and efficient detection and monitoring of the samples during the nucleic acid amplification process. Alternatively, the microcard may be used in a thermal cycling device that performs endpoint detection of the nucleic acid amplification of the samples. Several types of detection apparatus are shown in WO 02/00347A2 to Bedingham et al., the complete disclosure of which is hereby incorporated by reference for any purpose.

In various embodiments, the microcard may be configured to contact a sample block for thermally cycling the biological materials in the sample chambers of the microcard. The sample block may be operatively connected to a temperature control unit programmed to raise and lower the temperature of the sample block according to a user-defined profile. For example, in various embodiments, a user may supply data defining time and temperature parameters of the desired PCR protocol to a control computer that causes a central processing unit (CPU) of the temperature control unit to control thermal cycling of the sample block. Several non-limiting examples of suitable temperature control units for raising and lowering the temperature of a sample block for a microcard or other sample-holding member are described in U.S. Pat. No. 5,656,493 to Mullis et al. and U.S. Pat. No. 5,475,610 to Atwood et al., the disclosures of which are both hereby incorporated by reference for any purpose. Additional example of thermal cyclers used in PCR reactions include those described in U.S. Pat. No. 5,038,852 to Johnson et al. and U.S. Pat. No. 5,333,675 to Mullis et al., the contents of both of which are hereby incorporated by reference herein.

In various embodiments, the microcard comprises at least one fill chamber or reservoir, a plurality of sample chambers, and a network of fill conduits or channels connecting the reservoir and the plurality of sample chambers. The microcard may be made out of a material, such as polypropylene or polyethylene, that is suitable for PCR testing, but other materials may also be used that exhibit the proper characteristics of any material suitable for use in a PCR testing device.

One embodiment shown in FIGS. 1, 2, 3*a*-3*d*, and 4, provides a microcard 10 including two groups of reservoirs 14 divided into two groups X and Y. Reservoirs 14 each feed a plurality of sample chambers 12 via a network of fluid conduits 16 or channels. FIGS. 3*a*-3*d* depict a cross-section along line III-III of FIG. 2 through the center of one of sample chambers 12 of microcard 10. Microcard 10 comprises a first member 10*a*, a second member 10*b*, and a wall 20, as shown for example in FIGS. 3*a*-3*d*. Although in certain embodiments it may be desirable for microcard 10 to be formed in separate pieces, it may also be possible to form the microcard 10 as a single piece with either a hinge element or formed with a layering process.

FIG. 1 shows an embodiment of a microcard having 40 reservoirs and 384 sample chambers. In the embodiment shown, the sample chambers are positioned in a 16×24 matrices. The reservoirs are positioned in 2 rows—X and Y. In the embodiment shown, the first row Y comprises 16 reservoirs and the second row X comprises 24 reservoirs. Each reservoir positioned in the first row Y communicates with a horizontal row of sample chambers in a manner described in greater detail below, while each reservoir positioned in the second row X communicates with a vertical column of sample chambers in a manner described in greater detail below. It should be understood that the present teachings are suitable with any number of reservoirs and sample chambers.

In the embodiment shown in FIGS. 1, 2, 3*a*-3*d*, and 4, members 10*a* and 10*b* have a substantially rectangular shape, although other shapes compatible with a particular PCR testing device would also suffice. Additionally, members 10*a*, 10*b* and wall 20 may have a substantially similar size so that they may be easily aligned and mated together to form a microcard, although any other sizes and alignments of the members and wall may be used that remain compatible with a particular PCR testing device. Members 10*a*, 10*b* and wall 20 may be made out of a material, such as polypropylene, that is suitable for PCR testing, but other materials may also be used that are capable of providing the proper characteristics suitable for use in a PCR testing device. In various embodiments, the materials selected for members 10*a*, 10*b* and wall 20 may exhibit good water barrier properties, so that the microcard 10 will not leak even when subject to pressure. In other various embodiments, the materials selected for members 10*a*, 10*b*, and wall 20 may be transparent so that light may be transmitted across any portion of the members or wall.

Members 10*a*, 10*b* and wall 20 may be formed by any known processing method such as, but not limited to, molding, vacuum forming, pressure forming, and compression molding. A variety of such methods of forming members 10*a*, 10*b* and wall 20 together are further described in, for example, WO 02/01180A2 to Bedingham et al., the complete disclosure of which is hereby incorporated by reference for any purpose, and WO 02/00347A2 to Bedingham et al., incorporated herein above.

In the various embodiments, the thickness of the microcard, comprised of at least one member and wall, may vary with the volume of fluids to be processed, types of material to be processed, and other considerations related generally to standard PCR and other analytical procedures for biological materials. In one example of the embodiment shown in FIGS. 1, 2, 3*a*-3*d*, and 4, the thickness of the microcard 10, excluding the portions defining the chambers 12 and the reservoirs 14, may be between about 0.1 mm and about 10 mm, and in another example, between about 1.5 mm and about 2.0 mm. Again, however, these thicknesses of microcard 10 are only guidelines and not limitations on the present teachings.

Figure 2:
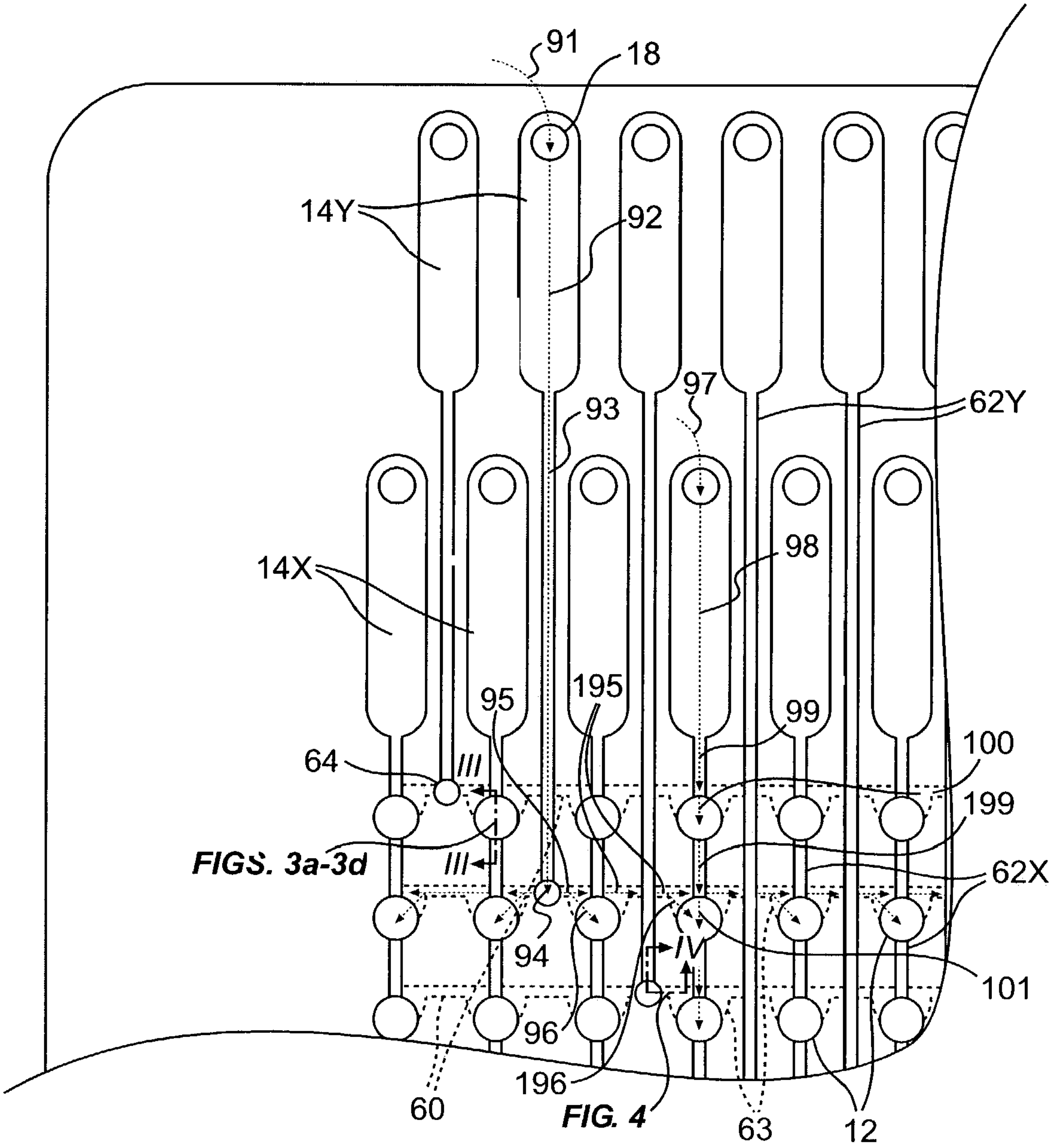
FIG. 2 is a magnified view of a portion of the microcard in FIG. 1 and illustrates two exemplary paths of fluid flow.

FIGS. 3*a*-3*d* depict a cross-section along line III-III of FIG. 2 through the center of one of sample chambers 12 of microcard 10. FIGS. 3*a*-3*d* show one of the plurality of sample chambers 12 divided into two chambers 12*a* and 12*b*. Member 10*a* comprises an outside surface 13 and an inside surface 17, and member 10*b* comprises an outside surface 21 and an inside surface 22, as labeled in FIG. 3*c*. Portions of 10*a* and 10*b* define portions of chambers 12, more specifically of chamber portions 12*a* and 12*b* respectively. FIGS. 3*a*-3*d* also show a chamber surface portion 15 of the inside surface 17 that defines a part of top chamber portion 12*a* of each of sample chambers 12, and a chamber surface portion 23 of the inside surface 22 that defines a part of bottom chamber portion 12*b* of each of sample chambers 12. Additionally, a channel surface portion 36 of the inside surface 17 of member 10*a* defines a portion of the channels in fluid communication with chamber portion 12*a*, as for example vertical channels 62X shown in FIG. 1. A channel surface portion 34 of the inside surface 22 of member 10*b* defines a portion of the channels in fluid communication with chamber portion 12*b*, as for example the horizontal channels 60 shown in FIG. 1. As here and throughout the present teachings, however, the relation of specific members to specific channels can be reversed and/or altered to any desirable geometric alignment. For example, the horizontal channels could be vertical channels, and the manner that these channels are in fluid communication with the chambers can be modified according to the manufacturing convenience and desired functionality of the microcard.

In various embodiments, the exact thickness of the members will vary with the volume of fluids to be processed, types of material to be processed, and other considerations related generally to standard PCR and other materials evaluation practices. However, in one example of the embodiment of FIGS. 1, 2, 3*a*-3*d*, and 4, the distance between the outside surface 13 and inside surface 17 of member 10*a*, excluding the portions defining the chamber surface portion 15 and channel surface portion 36, is between about 0.1 mm and about 10 mm, and in another example between about 0.2 mm and about 2.0 mm. Additionally, in another example of various embodiments, it may be desired that the distance between the outside surface 21 and inside surface 22 of member 10*b*, excluding the portions defining the chamber surface portion 23 and channel surface portion 34, be between about 0.1 mm and about 10 mm, and in another example between about 0.2 mm and about 2.0 mm. Again, however, these thicknesses of members 10*a* and 10*b* are only guidelines and not limitations on the present teachings.

In the embodiment of FIGS. 3*a*-3*d*, in order to adhere the members 10*a* and 10*b* to other surfaces, for example surfaces of a wall, it may be desirable to apply an adhesive to the inside surfaces 17 and 22 of members 10*a* and 10*b*. A variety of methods of adhering members in various embodiments are described in, for example, WO 02/01180A2 and WO 02/00347A2, incorporated herein above. To adhere members 10*a* and 10*b* to other surfaces it may be desirable to use an adhesive that would not react with the fluids 50 and 52 and/or be PCR compatible so as not to distort any readings from any devices used with the microcards. It may also be desired to apply the adhesive to only those portions of the inside surfaces 17 and 22 of members 10*a* and 10*b* that do not define other structures, such as the chamber surface portions 15 and 23 or the channel surface portions 36 and 34. In other various embodiments, however, any method of joining members to other surfaces is also acceptable. In this embodiment, it is also contemplated that the chamber surface portions 15 and 23 and/or the channel surface portions 36 and 34 be coated with a hydrophilic or any other type of coating that minimizes friction between these surface portions and the fluids 50 and 52 being introduced into the chamber portions 12*a* and 12*b*. However, in other various embodiments, such a coating is not necessarily desirable or needed. Finally, it may be desirable that the members 10*a* and 10*b* be configured so as not to inhibit fluid flow from reservoirs, as for example reservoirs 14 in FIG. 1, to the sample chambers 12. However, other various embodiments where the member configuration does inhibit fluid flow, for example due to geometry, material, or lack of a hydrophilic coating, are also contemplated.

In FIGS. 3*a*-3*d*, members 10*a* and 10*b* are separated by a wall 20 that passes through each of the sample chambers 12, dividing sample chambers 12 into two portions 12*a* and 12*b*. The term "wall" is intended to encompass any type of structure or material that could potentially separate members 10*a* and 10*b* and divide sample chamber 12 into two portions 12*a* and 12*b*. Other acceptable structures for which the term "wall" is intended to encompass include "membrane," "sheet," "lamina," "sheath," "film," or any other type of similar structures or materials that are not permeable. The wall may be formed of a material such as polypropylene, LEXAN, MYLAR or any other PCR compatible material capable of separating chamber portions, that also allows for breaching of the wall at least at the portions of the wall in contact with sample chamber portions 12*a* and 12*b*. The term "breach" or "breaching" is intended to encompass piercing, tearing, rupturing, breaking, dissolving, or to generally allow fluids to pass through. The step of breaching a wall configured to prevent fluid communication between the first fluid and the second fluid in the sample chamber, is also referred to as "initiating" at least one of the sample chamber portions so that the first and second fluids are in fluid communication with each other. In the embodiment illustrated, wall 20 is thinner than, but has roughly the same surface area as, each of members 10*a* and 10*b*. However, in various other embodiments involving divided chambers, the wall may be of smaller or larger in size as compared to the members, so long as it is still suitable for separating a plurality of chambers within the microcard. Other sizes and shapes, including individual walls for each chamber, may also be possible. As will be shown in FIGS. 8*a*-8*f*, which depict a cross-section along line VIII-VIII of FIG. 6 through the center of one of sample chambers 212 of microcard 210, a wall is not required for all of the various embodiments, as the present teachings also includes chambers that are not divided, and hence may not need a wall capable of separating the chambers. A variety of methods of forming walls are further described in, for example, WO 02/01180A2 and WO 02/00347A2, incorporated herein above.

As shown in FIGS. 3*a*-3*d*, wall 20 is a thin sheet having a top surface 20*a* and a bottom surface 20*b*. A portion of the top surface 20*a*, chamber surface portion 25, is exposed to and defines a part of chamber portion 12*a*, while a portion of bottom surface 20*b*, chamber surface portion 24, is exposed to and defines a part of chamber portion 12*b*. These chamber surface portions 24 and 25 may be thinner than the rest of the wall to more easily facilitate breaching. A channel surface portion 35 of the top surface 20*a* of wall 20 defines a portion of the channels in fluid connection with chamber 12*a*, for example vertical channels 62X shown in FIG. 1, while a channel surface portion 33 of the bottom surface 20*b* of wall 20 defines a portion of the channels, for example curved portion 63 of horizontal channels 60 shown in FIG. 1. As here and throughout these present teachings, however, the relation of specific members to specific channels can be reversed and/or altered to any desirable geometric alignment. For example, the horizontal channels could be vertical channels, and the manner that these channels are in fluid communication with the chambers can be modified according to the manufacturing convenience and desired functionality of the microcard.

In various embodiments that have divided chambers, the exact thickness of the wall will vary with the volume of fluids to be processed, types of material to be processed, and other considerations related generally to standard PCR and other analytical procedures for biological materials. However, in one example of the embodiment of FIGS. 3*a*-3*d*, the thickness of wall 20 (as measured between the top surface 20*a* and bottom surface 20*b*), excluding the portions defining the chamber surface portions 24 and 25, is between about 0.01 mm and about 10 mm, and in another example between about 0.1 mm and about 1.0 mm. In certain other embodiments, the thickness of the wall could also be tied to the thickness of either the overall microcard or its members. For example, the wall could make up between about 1% and about 99% of the thickness of the microcard 10, and in another example between about 10% and about 20%. Again, however, these thicknesses for walls are only guidelines and not limitations on the present teachings.

In FIGS. 3*a*-3*d*, members 10*a* and 10*b* are adhered to, or at least put into contact with, wall 20 by adhering inside surface 17 of member 10*a* to the top surface 20*a* of wall 20, while inside surface 22 of member 10*b* is adhered to the bottom surface 20*b* of wall 20. For this and various other embodiments, any method of joining the surfaces would be acceptable, including those previously described and incorporated above. In this embodiment, it is desirable that chamber surface portions 15 and 23 and channel surface portions 36 and 34, respectively of inside surfaces 17 and 22, respectively, not be adhered to wall 20. It is also contemplated that the portions of the wall 20 not in contact with members 10*a* and 10*b*, i.e., chamber surface portions 24 and 25 and/or channel surface portions 33 and 35, be coated with a hydrophilic or any other type of coating that minimizes friction between these surface portions and the fluids 50 and 52 being introduced into the chamber portions 12*a* and 12*b*. However in other embodiments, such a coating is not necessarily desirable or needed. Finally, in various embodiments it may be desirable that the wall be configured so as not to inhibit fluid flow from reservoirs to the sample chambers, for example, from reservoirs 14 to sample chambers 12 in the embodiment of FIGS. 1, 2, 3*a*-3*d*, and 4. However, other various embodiments where the member configuration does inhibit fluid flow, for example due to geometry, material, or lack of a hydrophilic coating, is also contemplated.

FIGS. 3*a*-3*d* show an example of a progression of one embodiment of the chamber during one contemplated use of the chamber Other various embodiments with geometric configurations and uses for the microcard are also possible. Sample chamber 12 is divided into two portions 12*a* and 12*b* that are separated by wall 20. The total volume of the chamber 12 in one example is between about 0.1 μL and about 1000 μL, and in another example between about 5 μL and about 10 μL, however, such a volume is only a guideline and not a limitation on the present teachings. In various embodiments, the volume will vary with the goals and objectives of the user. The total diameter of the chamber 12 in one example is between about 0.1 and about 100 mm, and in another example between about 1 and about 10 mm, however, such a diameter is only a guideline and not a limitation on the present teachings.

In FIGS. 3*a*-3*d*, top chamber portion 12*a* is defined by member 10*a* and wall 20, specifically the chamber surface portion 15 of the inside surface 17 of member 10*a* and the chamber surface portion 25 of the top surface 20*a* of wall 20. Bottom chamber portion 12*b* is defined by member 10*b* and wall 20, specifically the chamber surface portion 23 of the inside surface 22 of member 10*b* and the chamber surface portion 24 of the bottom surface 20*b* of wall 20. In both chamber portions 12*a* and 12*b*, the side portions of the chamber surface portions 15 and 23 of members 10*a* and 10*b* respectively are vertical, while the central portions of those surfaces 15 and 23 are curved. However, it is also contemplated that the chamber surface portions 15 and 23 have no vertical portion, and that the curved portion 26 of the outer surface 13 of member 10*a* is continuous with the rest of the outer surface 13.

Figure 3A:
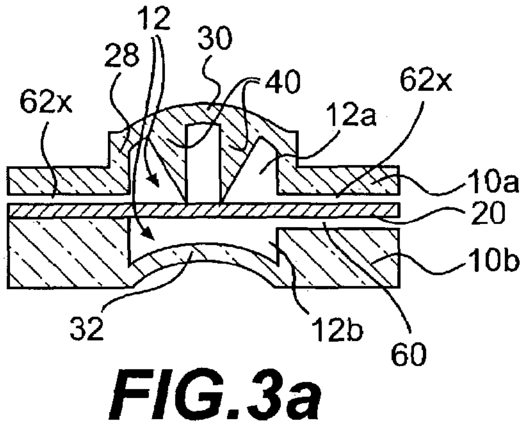
FIGS. 3*a*-3*d* are cross sections of a sample chamber of the microcard of FIG. 1 through a centerline of the sample chamber along line III-III of FIG. 2 and depict a sequence of operations to fill the sample chamber.
Figure 3B:
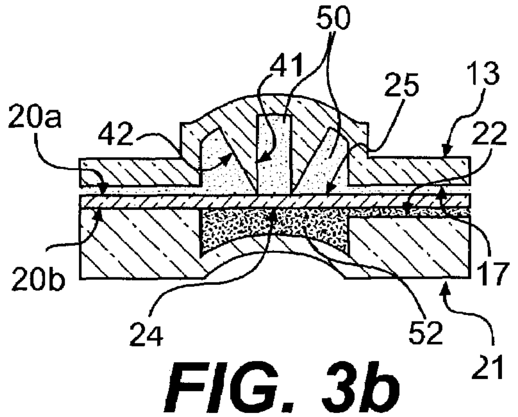
Figure 3C:
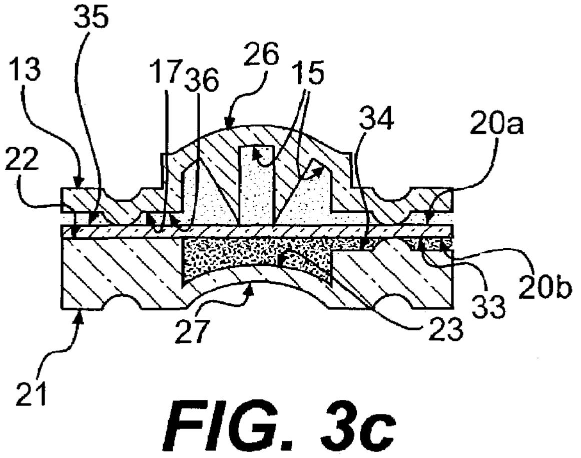
Figure 3D:
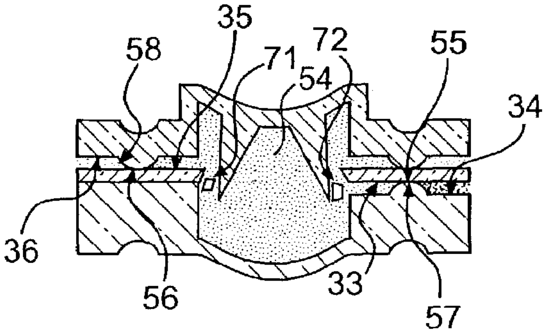

As shown in FIGS. 3*a*-3*c*, chamber portion 12*a* may be defined on one side by an outer convex or domed wall portion 30, which may include chamber surface portion 15 of inner surface 17 and curved chamber surface portion 26 of outer surface 13, without limitation to a specific size or shape for the wall portion 30. FIGS. 3*a*-3*d* also shows a vertical wall portion 28, but it is contemplated that such a portion 28 is not necessary and that the curved chambers surface portion 26 simply meet and be continuous with the rest of outer surface 13. The vertical wall portions 28 may be included, however, to increase the volume of both the chamber portion 12*a* and accordingly chamber 12. Chamber portion 12*b* may be defined by an inner concave or domed wall portion 32, which may include chamber surface portion 23 of inner surface 22 and curved chamber surface portion 27 of outer surface 21, without limitation to a specific size or shape. The bottom wall portion 32 may also be of roughly the same shape as top wall portion 30. In the illustrated embodiment, the top and bottom wall portions 30 and 32 are both curved in the same direction, however in other various embodiments their shapes need not be similar nor in the same direction. As seen in FIG. 3*d*, both wall portions 30 and 32 are flexible and of a thickness capable of inverting from their position in FIGS. 3*a*-3*c* to their position in FIG. 3*d*. The step of inverting the top and bottom wall portions from a first position to a second position is also referred to as "initiating" at least one of the sample chamber portions so that the first and second fluids are in fluid communication with each other. However, as will be seen in, for example FIGS. 8*a*-8*f*, it is also contemplated that some or all of the wall portions do not deform. The thickness of the wall portions 30 and 32 are similar, however, in various embodiments where the wall portions deform they are not required to be similar, and may vary in thickness with relation to each other as required by various processes that could cause the walls to invert from their position in FIGS. 3*a*-3*c* to their position form in FIG. 3*d*. The wall portions 30 and 32 have a thickness between about 0.01 mm and about 10 mm, with a thickness around 0.2 mm in one example. In various embodiments, the wall portions may also be a percentage of the thickness of either the microcard or the members between about 1% and about 99%. A wall portion thickness between about 5% and about 25% of the member and between about 2% and about 25% of the microcard are contemplated in this embodiment.

As shown in FIGS. 3*a*-3*d*, wall portion 30 of first member 10*a* may comprise at least one downward projection 40. In certain other embodiments where there are separate chambers, any number of projections is acceptable. FIGS. 3*a*-3*d* show an embodiment with two downward projections 40. It is also contemplated in various embodiments that no projections be in the chamber, especially where there are no separate chambers. Projections 40 are smaller in volume than the volume of chamber portion 12*a*. Put another way, projections 40 may be of any size and shape as long as it fits within chamber portion 12*a*. Projections 20 may be formed as a part of the wall portion 30 of first member 10*a*, as shown in FIGS. 3*a*-3*d*, or formed separately and later attached to the wall portion 30 of first member 10*a*. Specifically, the projection may be a portion of chamber surface 15 of inner surface 17 of member 10*a*. The projections 40 in FIGS. 3*a*-3*d* come to a point at or near the wall 20, but need not be of any particular shape or be in any particular location within the chamber portion 12*a*. The projections 40 may also come to an edge, as will be described below. In one example, the projections 40 are made of the same material as first member 10*a*, however, in various embodiments any material is satisfactory as long as it is capable of breaching through the wall 20. FIGS. 3*a*-3*d* show projection 40 comprising an inner edge 41 and an outer edge 42, with both edges meeting, as an example, at a point near or at the top surface 20*a* of wall 20. Inner edge 41 may be substantially perpendicular to the top surface 20*a* of wall 20, without limitation to a particular orientation of projections and edges with respect to any surfaces of member and wall.

As shown in FIGS. 3*b* and 3*c*, chamber portions 12*a* and 12*b* are filled with the desired sample fluids 50 and 52, respectively. The fluids in the various embodiments are transferred to chamber portions through the various channels and nodes via a method of filling, such as vacuum or centrifugal filling, or active or passive transport as known in the art of microfluidics. It should be understood that the method of filling may be varied and any specific method is only given as an exemplary method of filling. Once the chamber portions 12*a* and 12*b* are at least partially filled, the fill channels 60 and 62X of channel network 16 leading to the chamber portions 12*a* and 12*b* are staked or otherwise sealed off as shown in FIG. 3*c*. The term "staking", as used herein, may include, but is not limited to, using a device, such as a stylus, to deform a portion of the microcard to close or collapse a portion of the channel. Staking may also comprise utilizing an adhesive material such that when the channel is collapsed the two sides of the channel adhere to one another and block the flow through the channel. Staking with regards to this and other embodiments will be described more specifically later in the specification.

As shown in FIG. 3*d*, by inverting the concavity of the wall portion 30 through a pop or snap action, for example, projections 40 are forced downward to breach wall 20. The step of breaching the wall with projections forced downward is also referred to as "initiating" at least one of the sample chamber portions so that the first and second fluids are in fluid communication with each other. The step of "initiating" is not limited to the use of "projections," but encompasses any equivalent structures capable of "breaching" the wall as described herein, or other equivalents thereof. During the downward movement, the point formed by edges 41, 42 breaches wall 20 to remove the separation between sample chamber portions 12*a*, 12*b*, and break wall 20 into broken portions 71 and 72, although more broken portions are possible in this and other various embodiments. When this happens, for example, the wall portion 30 of member 10*a*, which may be defined by the curved chamber surface portion 26 of outer surface 13 and chamber surface portion 15 of inner surface 17, may go from being convex as in FIGS. 3*a*-3*c* to being concave as in FIG. 3*d*. Additionally, the wall portion 32 of member 10*b*, which may be defined by the curved chamber surface portion 27 of outer surface 21 and chamber surface portion 23 of inner surface 22, may go from being concave as in FIGS. 3*a*-3*c* to being convex as in FIG. 3*d*. Alternately, the wall portions 30 and 32 may take any other suitable shape. The step of changing the shape of the wall portions is also referred to as "initiating" at least one of the sample chamber portions so that the first and second fluids are in fluid communication with each other.

As shown in FIG. 3*d*, edges 41,42 of projection 40 may face away from the center of chamber 12 filled with composition 54, and cause broken portions 71 and 72 of wall 20 to spread apart so as to better allow fluids 50 and 52 to mix to form composition 54. Broken portions 71 and 72 of the wall 20 remain in chamber 12. In this embodiment, broken portions 71 and 72 are secured by projections 40 to avoid interfering with scanning of composition 54 in the central part of the chamber 12. In other various embodiments, additional means (such as, for example, longer projections 40 or a larger top chamber 12*a* as compared to bottom chamber 12*b*) may be utilized to prevent broken pieces from interfering with the scanning of composition 54. In various embodiments where wall 20 is composed of materials which do not interfere with scanning, the breached wall 20 may remain present in the chamber portion 12, regardless of whether there are broken pieces and where those broken pieces are located after breach. In various other embodiments, the wall may have some elastic properties that, when breached, causes the broken pieces to become flush with the sides of the chamber. Once wall 20 is breached, the sample fluids 50 and 52, which may, for example, comprise a fluid and a sample to be tested, flow together to form a composition 54 as shown in FIG. 3*d*. Upon mixing, the sample becomes ready for PCR cycling. By keeping the two fluids 50, 52 separate, microcard 10 may be filled with the desired fluids in advance of testing, and then combined at a desired time subsequent to the filling. This way, the user may fill the card in advance of performing the testing without concern of the materials reacting within the sample well.

In various embodiments utilizing a breach by inverting the concavity through a pop or snap action, the inversion can be accomplished in several ways, a few examples of which are disclosed below. For example, domed portions 30, 32 may be moved from their initial position in FIGS. 3*a*-3*c* to the position that cause breaching of wall 20, in FIG. 3*d*, by applying force to one or both of portions 30, 32. In another example, a vacuum could be applied to at least the domed chamber surface portion 27 of outer surface 21 of wall portion 32 of member 10*b* that would create suction and cause wall portion 32 to invert. The inversion of portion 32 may then, due to the sealed nature of chamber portions 12*a* and 12*b*, pull wall portion 30 causing it to invert, which would then cause projections 40 to pierce wall 20. Another embodiment for a method of inversion applies force to the curved chamber surface portion 26 of outer surface 13 of wall portion 30, thus causing it to invert and cause projections 40 to pierce wall 20 due to projections and/or increased fluid pressure in chamber portion 12*a* (specifically on the top surface 20*a* of wall 20) and, due to the sealed nature of chamber portions 12*a* and 12*b*, cause wall portion 32 to invert. In one example, the pressure can be applied by a separate microcard holder with protrusions which cause inversion. The holder can be configured to remain with the microcard during thermocycling and scanning. In another method, a heat source is applied to the curved chamber surface portion 26 of outer surface 13 of wall portion 30 causing the wall portion to deform in the direction opposite to the heat source, and in this way the wall portion 30 becomes inverted. In other embodiments, the wall portion 30 is made of a material that is sensitive to heat and/or electrical current, where application of such to wall portion 30 causes inversion. For example, wall portion 30 can be made of nitinol, other alloys, or polymers known in the art of shape-memory materials. The steps of applying a force to a sample chamber portion, heating a sample chamber portion, and applying a vacuum to a sample chamber portion, are each individually also referred to as "initiating" at least one of the sample chamber portions so that the first and second fluids are in fluid communication with each other.

Figure 5B:
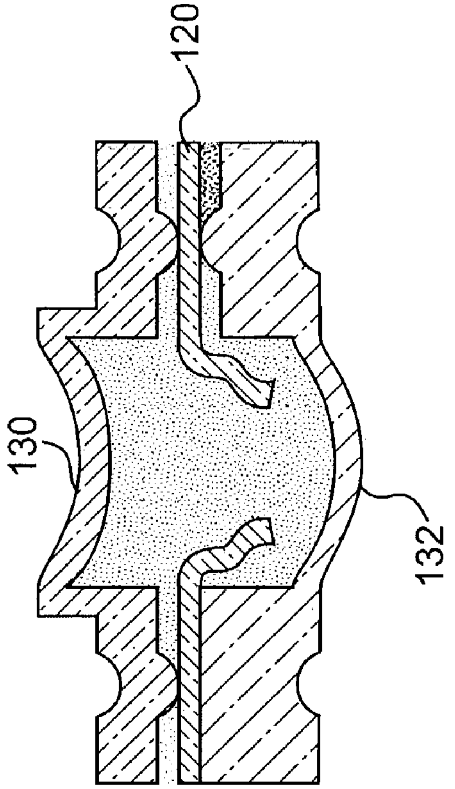
FIGS. 5*a*-5*b* are cross sections through a center line of another embodiment of a single chamber that could be incorporated into the microcard of FIG. 1.
Figure 5A:
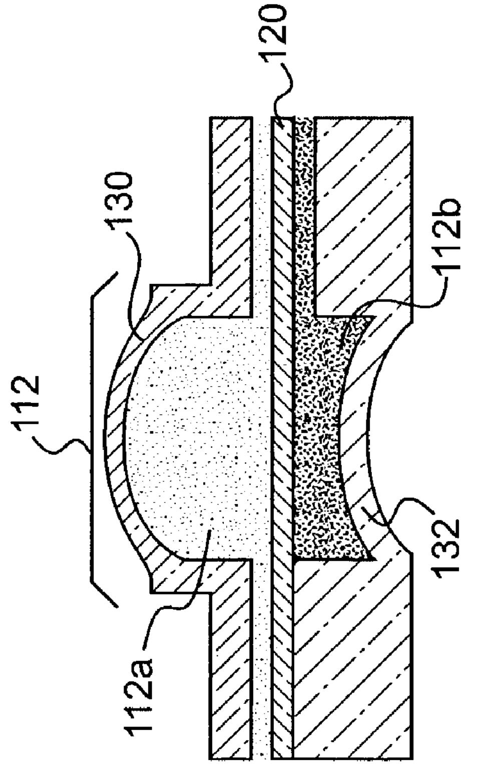

FIGS. 5*a*-5*b* illustrate another embodiment of breaching the wall through the use of fluid pressure for inversion. Sample chamber 112 is divided into chamber portions 112*a* and 112*b*. Unlike other embodiments, sample chamber 112 does not include projections to breach wall 120. Instead, wall 120 is configured to breach by the pressure exerted on it by the fluid contained within chamber portions 112*a* and 112*b* when the walls 130 and 132 are inverted to the position shown in FIG. 5*b*. The wall 120 of this embodiment can be similar to, be thinner than, or be made of a material that is more easily breachable than other embodiments. Chamber portions 112*a* and 112*b* may be inverted in a manner similar to that described above, or by any other acceptable method. The step of inverting the chamber portions is also referred to as "initiating" at least one of the sample chamber portions so that the first and second fluids are in fluid communication with each other.

In another embodiment (not pictured), a wall may be used to separate two sample chamber portions such that at least the portion of the wall in contact with the two sample chamber portions degrades under predetermined conditions, such as upon reaching a certain temperature, and allows for the two chamber portions to become one integrated chamber. With such an embodiment, no movement of the chamber portions would be necessary, thus many other chamber and microcard configurations become possible for other embodiments. The step of degrading the wall configured to prevent fluid communication between the first fluid and second fluid in the sample chamber, is also referred to as "initiating" at least one of the sample chamber portions so that the first and second fluids are in fluid communication with each other.

FIG. 1 discloses one embodiment of laying out the chambers 12 on microcard 10. In other various embodiments, other geometric layouts of chambers are possible that would result in a usable microcard consistent with the present teachings. FIG. 1 discloses a top view of microcard 10 with member 10*a* in direct view, and members 10*b* and wall 20 being disposed underneath member 10*a*. Disposed on one side of the microcard in FIG. 1 are a plurality of reservoirs 14. In various embodiments, a member may define all or part of the reservoirs, however, the reservoirs may be defined by other members or by a wall and may be placed on any portion of the microcard. Reservoir 14, as depicted here, has an elongated shape capable of containing a suitable amount of sample fluids to be distributed to a desired number of chambers 12. However in other various embodiments, the reservoir may of any size and shape. Reservoir 14 includes a fill opening 18 through which a user may introduce sample fluid by, for example, use of a pipette.

In another embodiment, the sample fluid may be introduced into reservoir 14 via active or passive transport known in the art of microfluidics. The fill opening can be of any size and shape, but may be smaller in size than the reservoir. The reservoir 14 may be defined by any or all of portions of member 10*a*, member 10*b*, and wall 20. However, any reservoir configured to allow fluid flow into the various channels is contemplated.

Figure 6:
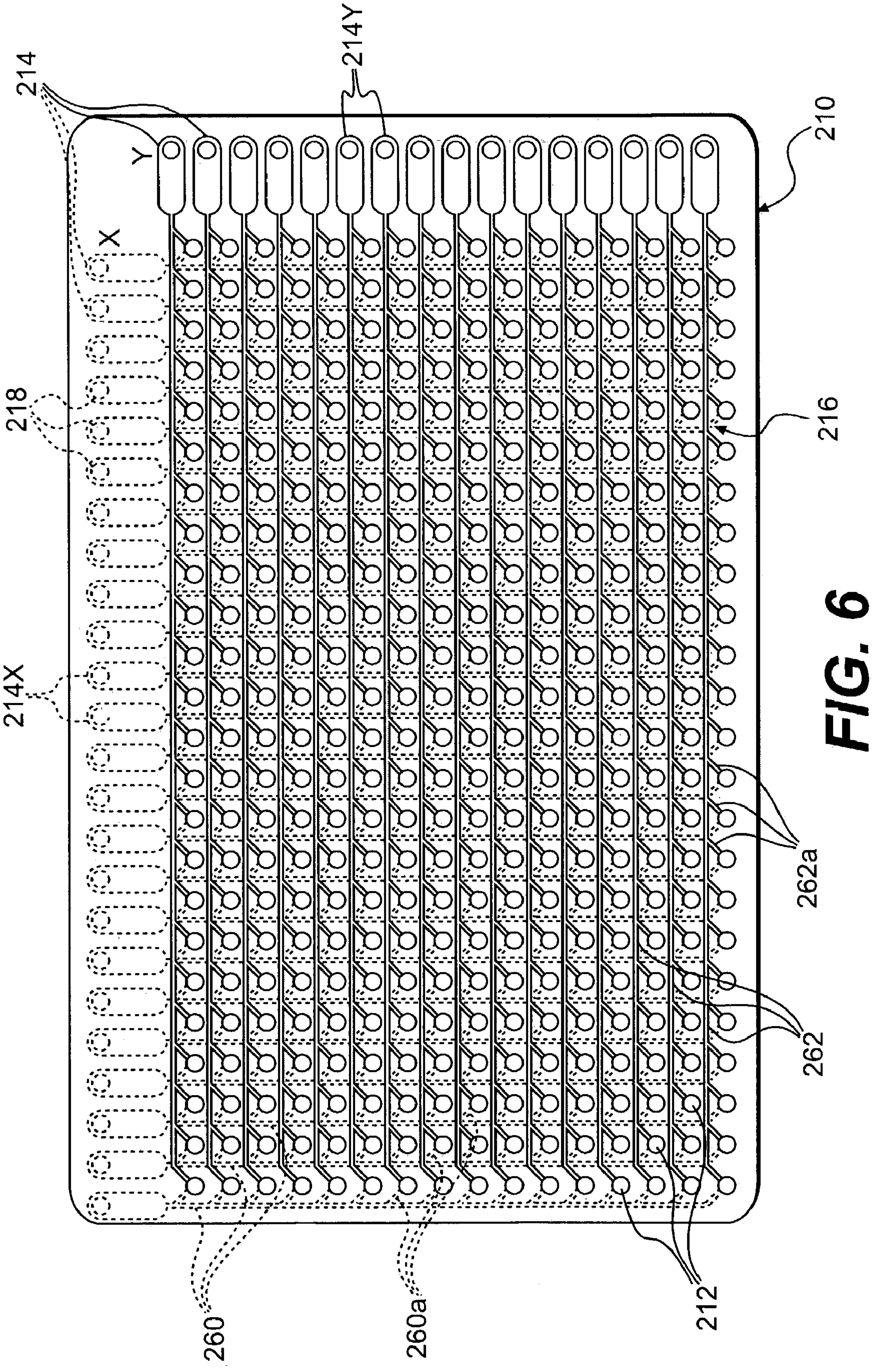
FIG. 6 is a plan view of another exemplary embodiment of a microcard.

As shown in FIG. 1, reservoir 14 is connected to a network of fluid channels 16 that are in turn connected to chambers 12. The chambers disclosed in FIGS. 3*a*-3*d* and FIGS. 5*a*-5*b* are exemplary embodiments of chambers in microcard 10 in FIG. 1, and do not in anyway limit the microcard embodiment described in FIG. 1. The orientation of the channels in FIG. 1 does not need to be physically compatible with the exemplary embodiments of a chamber. The networks 16 disclosed in FIG. 1 comprise a plurality of horizontal channels 60, a plurality of feeder channels 62Y, and a plurality of vertical channels 62X. The terms "horizontal" and "vertical" are merely used for convenience to describe networks 16 as depicted in FIG. 1 and are not intended to convey any required configuration of the microcard. As embodied herein, microcard 10 defines 384 sample chambers 12 with 16 rows and 24 columns. It should be understood that a wide variety of configurations are possible, such as the configuration shown in FIG. 6. In various embodiments, a first network of a plurality of horizontal channels and a second network of a plurality of vertical channels are positioned on substantially parallel planes, respectively, as illustrated in FIGS. 1 and 6 by broken and solid lines.

Figure 4:
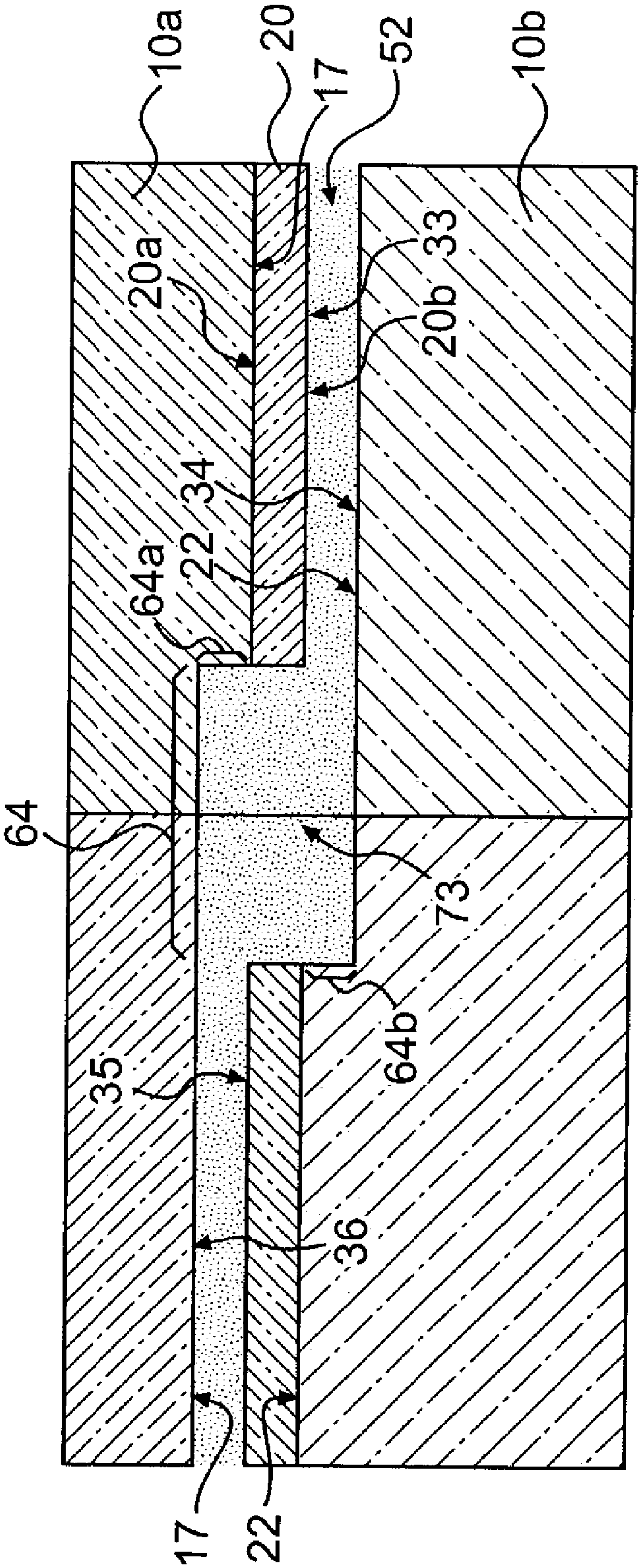
FIG. 4 is a cross section of a sample node of the microcard of FIG., 1 through a centerline of the sample node along line IV-IV of FIG. 2.

The first row of reservoirs 14Y are in fluid connection through feeder channels 62Y and node 64 to horizontal channels 60, while second row of reservoirs 14X are in direct fluid connection with vertical channels 62X, as best shown in FIGS. 1 and 2. An example of a node is depicted in FIG. 4. Reservoirs 14Y are in fluid connection with a chamber portion, for example chamber portion 12*b*, disposed on member 10*b*, while reservoirs 14X are in fluid connection with a chamber portion, for example chamber portion 12*a*, disposed on member 10*a*. However, reservoir 14X is not in direct fluid connection with each chamber portion 12*a* through vertical channel 62X, but instead the first portion of vertical channel 62X-1 directly connects the reservoir 14X to first chamber portion 12*a*-1, and through that first chamber portion 12*a*-1 connects with the next vertical channels portion 62X-2 to the next chamber portion 12*a*-2 and so on. As shown in FIGS. 1 and 4, the vertical channels 62X, the feeder channels 62Y, and the top portion 64*a* of node 64 are defined by member 10*a* and wall 20. Specifically, the vertical channels 62X, the feeder channels 62Y, and the top portion 64*a* of node 64 are defined on one side by the channel surface portion 36 of the inner surface 17 of member 10*a*, and on the other side by the channel surface portion 35 of the top surface 20*a* of wall 20.

In FIGS. 1, 2, 3*a*-3*d* and 4, the horizontal channels 60 and bottom portion 64*b* of node 64 are defined on one side by the channel surface portion 34 of the inner surface 22 of member 10*b*, and on the other side by the channel surface portion 33 of the bottom surface 20*b* of wall 20. Unlike vertical channels 62X, however, in this embodiment the horizontal channels 60 do not connect intervening chamber portions 12*b*, but are contiguous channels in series with curved channel portions 63 that provide fluid connection between horizontal channels 60 and all chamber portions 12*b*. Additionally, the top portion 64*a* and bottom portion 64*b* of node 64 are in fluid connection with each other through a hole 73 in wall 20, as shown in FIG. 4. FIG. 4 depicts a cross-section along line IV-IV of FIG. 2 through the center of one of sample chambers 12 of microcard 10. Thus, before wall 20 is breached, the portion of network 16 that includes channels 60 and 62Y which are in fluid communication with reservoirs 14Y of group Y, are completely isolated from the portion of network 16 that includes channels 62X which are in fluid communication with reservoirs 14X of group X.

Thus, in FIG. 1, to fill the top chamber portion 12*a*, a user would fill reservoirs 14X, through fill opening 18, with either the same or different fluids 50. The fluids would then flow through vertical channels 62X into the top chamber portions 12*a* of chamber 12. More specifically, the fluid 50 would flow through the first part of vertical channel 62X-1 into the first top chamber portion 12*a*-1, and if there was a further vertical channel 62X-2 on the opposite side of first top chamber portion 12*a*-1, the fluid would flow into that further vertical channel 62X-2 until it reached where either vertical channel 62X-n was full, or chamber portion 12*a-n* was full. To fill the bottom chamber portion 12*b*, a user would fill reservoirs 14Y through fill opening 18 with either the same or different fluids 52, and cause the fluids to flow through feeder channels 62Y to the top portion 64*a* of node 64 through the hole 73 in the wall 20 into the bottom portion 64*b* of node 64. An example of a node is depicted in FIG. 4. From there, the fluid 52 would flow into the horizontal channel 60 and through curved channel portion 63 into the bottom chamber portion 12*b*. This latter step occurs for all of the bottom chamber portions 12*b* disposed on microcard 10. The fluids in the various embodiments are transferred to chamber portions through the various channels and nodes via a known method of filling, such as vacuum or centrifugal filling, or active or passive transport as known in the art of microfluidics. It should be understood that this method of filling may be varied and is only given as an exemplary method of filling.

An exemplary method of filling the microcard of FIG. 1 is also shown in FIG. 2. There, filling step 91 shows a fluid being placed into a fill opening 18 of a reservoir 14Y. Flowing step 92 then shows the fluid flowing through the reservoir 14Y until it reaches the feeder channel 62Y and then flows through the feeder channel 62Y, in flowing step 93, into the node 64. In flowing step 94, the fluid passes through the wall by the way of a hole in the node 64 into a horizontal channel 60. Flowing step 95 shows the fluid flowing through the horizontal channel 60. The fluid then diverges. Some of the fluid flows into a sample chamber portion 12 in flowing step 96, while some of the fluid continues flowing down the horizontal channel 60 in flowing step 195. The fluid that continues to flow through the horizontal channel 60 can then enter any of the successive sample chamber portions 12 in flowing step 196. For the vertical channels 62X and their respective chambers 12, filling step 97 shows a fluid being placed into a fill opening 18 in reservoir 14X. Flowing step 98 then shows the fluid flowing down the reservoir 14X until it reaches a vertical channel 62X, and then flows into and through the vertical channel 62X in flowing step 99. At the end of the first vertical channel portion, in flowing step 100, the fluid flows into first sample chamber portion. Some of the fluid stays in the chamber 12, but most of the fluid will continue to flow into the next vertical channel portion in flowing step 199. From there, the fluid flows into the next sample chamber portion in flowing step 101, and the process continues for the rest of the vertical channel portions and sample chamber portions.

Once the chamber portions 12*a* and 12*b* on microcard 10 have been filled, as shown in the progression of FIGS. 3*a* and 3*b*, the channels 60 and 62X may be staked, an example of which is shown in FIG. 3*c*. For the microcard 10 disclosed in FIG. 1, one method of staking is to run a knife-like structure between the successive rows of horizontal and vertical chambers 12 and collapse the channels 60 and 62X. For channels 62X, a staked portion 58 of the channel surface portion 36 of the inner surface 17 of member 10*a* would come into contact with a staked portion 56 of the channel surface portion 35 of the top surface 20*a* of wall 20. For channels 60, a staked portion 57 of the channel surface portion 34 of the inner surface 22 of member 10*b* would come into contact with a staked portion 55 of the channel surface portion 33 of the bottom surface 20*b* of wall 20. In this way, each chamber would no longer be in fluid communication with either the reservoirs 14 or other chambers 12. Other methods of staking are possible, and this particular method is only exemplary and is not meant as a limitation on the present teachings. Once staked, the step of inverting the cavity to cause the fluids 50 and 52 in chamber portions 12*a* and 12*b* to mix is described above in connection with FIGS. 3*a*-3*d*. The microcard with its chambers 12 filled with composition 54 is now ready for further processing. In various embodiments, depending on the configuration and the geometry of the chambers and microcards, other methods of loading the microcard with fluids are possible.

As shown in FIG. 1, network 16 may be configured so that each reservoir is in communication with only one row or column. In this manner, reservoir 14Y of reservoirs 14 only communicates with the first row of chambers 12. Reservoir 14X of reservoirs 14 only communicates with the first column of chambers 12. Through such a configuration, it is possible to fill each of the X and Y reservoirs with a different fluid, if desired. In the configuration shown in FIG. 1, there are 16 Y reservoirs and 24 X reservoirs, which would allow for 386 different samples to be tested at the same time, if desired. Other combinations would also be possible, such as placing the same fluid in all of the Y reservoirs and a different fluid in each of X reservoirs thus creating 24 different reactions each with 16 replicates. As can be seen, the configuration of the network of channels 16 and their communication with reservoirs 14 for great flexibility by a user to configure the card for a variety of different testing configurations. For example, reservoir 14Y could actually be two reservoirs for which two different fluids are added and then mixed by having them run into a single feeder channel 62Y.

As mentioned above, the microcard may have other configurations including but not limited to the number of sample chambers and reservoirs as, for example, in FIG. 1. In another embodiment depicted in FIG. 6, a microcard 210 is shown having a different configuration of reservoirs 214, each having a fill port 218, and a network of fluid conduits or channels 216. Each reservoir 214 of the X group is in fluid communication with a vertical column of sample chambers 212 via a main fluid channel 260 that branches off to individual sample chambers 212 via branch channels 260*a*. In this embodiment, main channel 260 is vertical with branch channels 260*a* running diagonally off of it to the chamber 212. Specifically, the branch channel 260*a* is in fluid connection with the main channel 260, and both main channel 260 and branch channel 260*a* are disposed on the bottom part of the microcard, hence the dotted lines. Thus, a fluid in this embodiment would flow through reservoir opening 218 into the reservoir 214X, which is disposed on the bottom member 210*b* of the microcard 210, through the wall 220 into the main channel 260, into a branch channel 260*a* and into a chamber 212 or chamber portion. In a similar fashion, each reservoir 214 of the Y group is in fluid communication with a horizontal row of sample chambers 212 via a main fluid channel 262 that branches off to individual sample chambers 212 via branch channels 262*a*. In this embodiment, main channel 262 is horizontal with branch channels 262*a* running diagonally off of it to the chamber 212. Specifically, the branch channel 262*a* is in fluid connection with the main channel 262 and disposed on the top part of the microcard. Thus, a fluid Y in this embodiment would flow through reservoir opening 218 into the reservoir 214Y, which is disposed on the top member 210*a* of the microcard 210, into the main channel 262, through the branch channel 262*a* and into a chamber 212 or chamber portion. It is also contemplated that both of the reservoirs 214X and 214Y be disposed on the top part or top member 210*a* of the microcard 210. In that embodiment, the reservoir 214X on the top member would be in fluid communication with main channel 260 on the bottom member through a node that comprises a hole in wall 220, similar but not necessarily limited to the node 64 described in FIGS. 1 and 4. In that embodiment, it may be desirable to place the node between the reservoir 214X and the first branch channel 260*a*.

Figure 7:
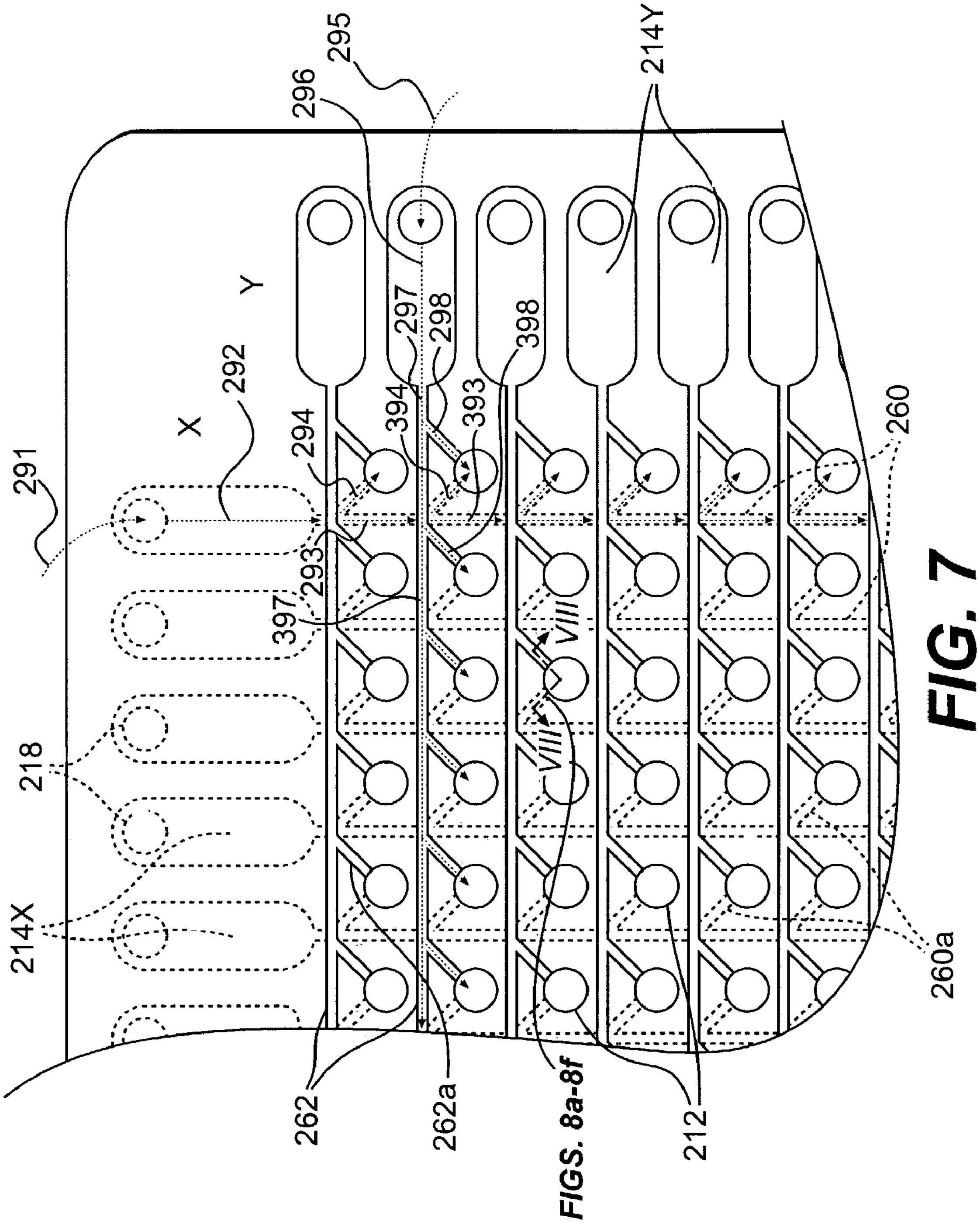
FIG. 7 is a magnified view of a portion of the microcard in FIG. 6 and illustrates two exemplary paths of fluid flow.

An exemplary method of filling the microcard of FIG. 6 is shown in FIG. 7. There, filling step 291 shows a fluid being placed into a fill opening in row X. Flowing step 292 then shows the fluid flowing through the reservoir until it reaches the vertical channel and then flows through the vertical channel, in flowing step 293. From there, the fluid flow diverges. Some of the fluid will flow through the branch channel into the first sample chamber in flowing step 294, but most of the fluid will continue to flow through the vertical channel as in flowing step 393. At each successive branch channel, as shown in flowing step 394, some of the fluid will flow through the branch channel into the sample chamber. For the horizontal channels and their respective chambers, filling step 295 shows a fluid being placed into a filling opening in row Y. Flowing step 296 then shows the fluid flowing through the reservoir until it reaches a horizontal channel, and then flows into and through the horizontal channel in flowing step 297. From there, the fluid flow diverges. Some of the fluid will flow through the branch channel into the first sample chamber in flowing step 298, but most of the fluid will continue to flow through the vertical channel as in flowing step 397. At each successive branch channel, as shown in flowing step 398, some of the fluid will flow through the branch channel into the sample chamber.

In various embodiments, sample chambers 212 could be divided by a wall (not shown) into two sample chamber portions, however, as seen in other various embodiments, as illustrated in FIGS. 8*a*-8*f*, the chamber may have only one chamber portion that does not require a separating wall. The part of network 216 in communication with the X reservoirs would fill one of the two sample chamber portions of each of the chambers 212 and the part of network 216 in communication with the Y reservoirs would fill the other sample chamber portion of each of the chambers 212. Chambers 212 could have any of the configurations described above that would allow for breaching of the wall to unite the two sample chamber portions into a single sample chamber. However, once again, in various other embodiments, the microcard could have a plurality of unseparated chambers that combine the same or different fluids using the method outlined above or other methods. All the variations with regards to parts of the microcard 10 in FIG. 1 is hereby incorporated into the microcard 210 in FIG. 6, another embodiment. For example, all the variations regarding the members 10*a* and 10*b* are imparted on members 210*a* and 210*b*. The chambers 212 in FIG. 6 may be configured like the chambers 12 and 112 described in FIGS. 3*a*-3*d* and FIGS. 5*a*-5*b*, however other configurations of chambers are also acceptable.

Figure 8A:
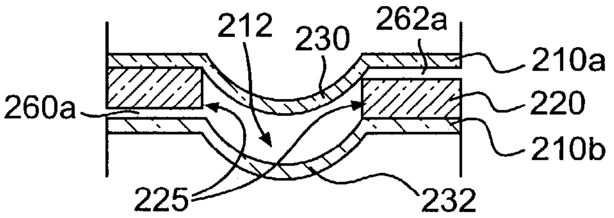
FIGS. 8*a*-8*f* are cross sections of another sample chamber that could be used with the microcard of FIG. 6 through a centerline of the sample chamber along line VIII-VIII of FIG. 7 and depict a sequence of operations to fill the sample chamber.
Figure 8B:
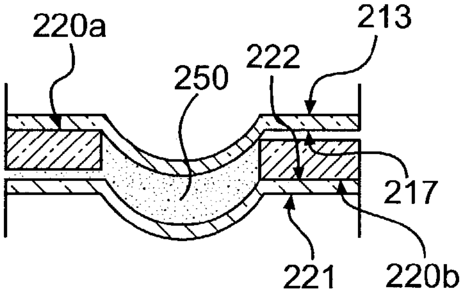
Figure 8C:
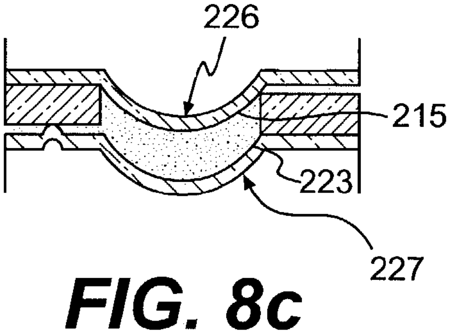
Figure 8D:
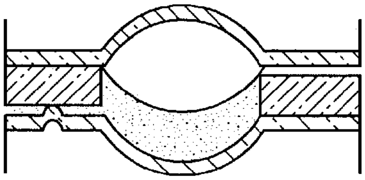
Figure 8E:
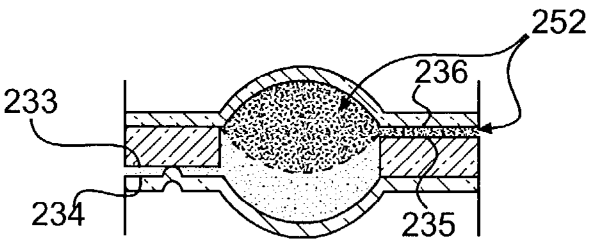
Figure 8F:
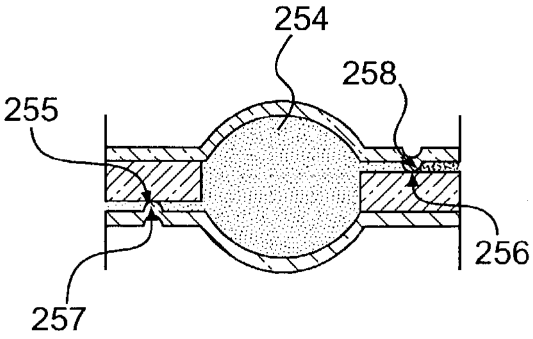

In various embodiments, the microcard illustrated in FIG. 6 comprises chamber 212 illustrated in FIGS. 8*a*-8*f*. FIGS. 8*a*-8*f* depict a cross-section along line VIII-VIII of FIG. 6 through the center of one of sample chambers 212 of microcard 210. FIGS. 8*a*-8*f* show a chamber 212 with first member 210*a*, a second member 210*b*, and a wall 220 disposed between portions of the members. In the illustrated embodiment, the wall 220 is thicker than members 210*a* and 210*b*, and consequently gives more structural support to the chamber 212. FIGS. 8*a*-8*f* show member 210*a* comprising an outside surface 213 and an inside surface 217, and member 210*b* comprising an outside surface 221 and an inside surface 222. Portions of 210*a* and 210*b* define portions of chambers 212. In FIGS. 8*a*-8*c*, the portions of 210*a* that define portions of chambers 212 are concave, and the portions 210*b* that define portions of chambers 212 are convex. In FIGS. 8*d*-8*f*, the portions of 210*a* that define portions of chambers 212 are convex, and the portions 210*b* that define portions of chambers 212 are also convex. Chamber 212 can be characterized as having chamber portions even if it is one continuous chamber. For instance, there can be an upper half of the chamber, a lower half, center of the chamber, and along the first or second members of the chamber. A chamber surface portion 215 of the inside surface 217 defines a top part of sample chambers 212, while a chamber surface portion 223 of the inside surface 222 defines a bottom part of sample chambers 212. Additionally, a channel surface portion 236 of the inside surface 217 of member 210*a* defines a portion of the channel in fluid connection with the chamber, as for example portion 262*a* of the channels 262 shown in FIG. 6, while a channel surface portion 234 of the inside surface 222 of member 210*b* defines a portion of the channel in fluid connection with the chamber, as for example portion 260*a* of the channels 260 shown in FIG. 6. As here and throughout these present teachings, however, the relation of specific members to specific channels can be reversed and/or altered to any desirable geometric alignment.

In various embodiment, the exact thickness of the members will vary with the volume of fluids to be processed, types of material to be processed, and other considerations related generally to standard PCR and other materials evaluation practices. However, in one example of the embodiment of FIGS. 6 and 8*a*-8*f*, the distance between the outside surface 213 and inside surface 217 of member 210*a*, excluding the portions defining the chamber surface portion 215 and channel surface portion 236, may be between about 0.01 mm and about 10 mm, and in another example between about 0.1 mm and about 1.0 mm. Additionally, in one example of this embodiment, the distance between the outside surface 221 and inside surface 222 of member 210*b*, excluding the portions defining the chamber surface portion 223 and channel surface portion 234, may be between about 0.01 mm and about 10 mm, and in another example between about 0.1 mm and about 1.0 mm. Again, however, these thicknesses of members 210*a* and 210*b* are only guidelines and not limitations on the present teachings.

In the embodiment of FIGS. 8*a*-8*f*, in order to adhere the members 210*a* and 210*b* to other surfaces, it may be desirable to apply an adhesive to the inside surfaces 217 and 222 of members 210*a* and 210*b*. For this and various other embodiments, any method of joining the surfaces would be acceptable, including those previous described and incorporated above. One method of adhering the members 210*a* and 210*b* to other surfaces may be use an adhesive that would not react with the fluids 250 and 252 and/or be PCR compatible so as not to distort any readings. Another method of adhering would be to apply the adhesive to only those portions of the inside surfaces 217 and 222 of members 210*a* and 210*b* that do not define other structures, such as the chamber surface portions 215 and 223 or the channel surface portions 236 and 234. Any other methods of joining members 210*a* and 210*b* to other surfaces, however, are also acceptable. In this embodiment, it is also contemplated that the chamber surface portions 215 and 223 and/or the channel surface portions 236 and 234 be coated with a hydrophilic or any other type of coating that minimizes friction between these surface portions and the fluids 250 and 252 being introduced into the chamber 212. However, such a coating is not necessarily desirable or needed. Finally, it may be desirable that the members be configured so as not to inhibit fluid flow from reservoirs to the sample chambers, as for example reservoirs 214 to the sample chambers 212 in FIG. 6.

In the embodiment shown in FIGS. 8*a*-8*f*, members 210*a* and 210*b* are separated by a wall 220 that, unlike the previous embodiments, does not pass through each of the sample chambers 212. In other embodiments, it may be possible that there is no wall at all, and that members 210*a* and 210*b* are in direct contact with each other. Wall 220 may be formed of a material such as polypropylene, LEXAN, MYLAR or any other PCR compatible material capable of separating members 210*a* and 210*b* and providing structural support. Wall 220 may be the same size and shape as each of portions 210*a* and 210*b*, but it may be of a different size in other various embodiments. A variety of methods of forming walls are further described in, for example, WO 02/01180A2 and WO 02/00347A2, incorporated herein above. As shown in FIGS. 8*a*-8*f*, wall 220 has a top surface 220*a*, a bottom surface 220*b*, and chamber surface portions 225. In this embodiment, chamber surface portion 225, is exposed to and defines a side portion of chamber 212. Additionally, a channel surface portion 235 of the top surface 220*a* of wall 220 defines a portion of the channel in fluid communication with chamber 212, for example portion 262*a* of vertical channels 262 shown in FIG. 6, while a channel surface portion 233 of the bottom surface 220*b* of wall 220 defines a portion of the channel in fluid communication with chamber 212, for example a portion 260*a* of horizontal channels 260 shown in FIG. 6. As here and throughout these present teachings, however, the relation of specific members to specific channels can be reversed and/or altered to any desirable geometric alignment.

In various embodiments, the exact thickness of the wall will vary with the volume of fluids to be processed, types of material to be processed, and other considerations related generally to standard PCR and other materials evaluation practices. However, in this embodiment, the distance between the top surface 220*a* and bottom surface 220*b* of wall 220, excluding the portions defining the chamber surface portions 225, is between about 0.01 mm and about 10 mm, and in another example between about 0.1 mm and about 1.0 mm. The thickness of the wall could also be tied to the thickness of either the overall microcard or members. In one example of this embodiment, the wall 220 could make up between about 1% and about 99% of the thickness of the microcard 210, and in another example between about 25% and about 75%. Alternately, the wall 220 could make up between about 1% and about 1000% of the thickness of the members 210*a* and 210*b* individually, and in another example between about 50% and about 150%. Again, however, these thicknesses for walls are only guidelines and not limitations on the present teachings.

In the embodiment of FIGS. 8*a*-8*f*, members 210*a* and 210*b* are adhered to, or at least put into contact with, wall 220 by adhering inside surface 217 of member 210*a* to the top surface 220*a* of wall 220, while inside surface 222 of member 210*b* is adhered to the bottom surface 220*b* of wall 220. For this and various other embodiments, any method of joining the surfaces would be acceptable, including those previously described and incorporated above. It may desirable that chamber surface portions 215 and 223 and channel surface portions 236 and 234, respectively of inside surfaces 217 and 222, not be adhered to wall 220. In this embodiment, it is also contemplated that the portions of the wall 220 not in contact with members 210*a* and 210*b*, i.e., chamber surface portions 225 and/or channel surface portions 235 and 233, be coated with a hydrophilic or any other type of coating that minimizes friction between these surface portions and the fluids 250 and 252 being introduced into the chamber 212. However, such a coating is not necessarily desirable or needed in other various embodiments. Finally, it may be desirable in this embodiment that the wall 220 be configured so as not to inhibit fluid flow from reservoirs to the sample chambers, for example reservoirs 214 to chambers 212 in FIG. 6. However, in other embodiments, a wall configuration that inhibits fluid flow is also contemplated.

The embodiment in FIGS. 8*a*-8*f* show an example of a progression of the chamber during one contemplated use of the chamber. Other geometric embodiments consistent with the present teachings are also possible. In one example, the total volume of the chamber 212 is between about 0.1 μL and about 1000 μL, and on another example between about 5 μL and about 10 μL, however, such a volume is only a guideline and not a limitation on the present teachings. The total diameter of the chamber 212 is between about 0.1 mm and about 100 mm, and between about 1 mm and about 10 mm, however, such a diameter is only a guideline and not a limitation on the present teachings. Chamber 212 is defined by member 210*a*, member 210*b* and wall 220, specifically the chamber surface portion 215 of the inside surface 217 of member 210*a*, the chamber surface portion 223 of the inside surface 222 of member 210*b*, and the chamber surface portion 225 of the wall 220. The side portions of chamber 212, which are defined by chamber surface portions 225 of wall 220, are vertical, while the central portions of chamber surface portions 215 and 223 are curved. However, it is also contemplated in other embodiments that the chamber surface portions may have vertical portions, and that the curved portions of the outer surfaces may not be flush with the rest of the outer surfaces. The vertical portions in other embodiments could serve to increase the volume or obtain an advantageous geometry for a particular use.

As shown in FIGS. 8*a*-8*c*, chamber 212 may be defined on top by an inner concave or domed wall portion 230, which may be defined by chamber surface portion 215 of inner surface 217 and curved chamber surface portion 226 of outer surface 213, without limitation to a specific size or shape. Chamber 212 may be defined on the bottom by an outer convex or domed wall portion 232, which may be defined by chamber surface portion 223 of inner surface 222 and curved chamber surface portion 227 of outer surface 221, without limitation to a specific size or shape. The embodiment also provides that the bottom wall portion 232 is of roughly the same shape as top wall portion 230. While it is contemplated that the top and bottom wall portions 230 and 232 should both-be curved in the same direction, their shapes need not be similar on other various embodiments. As seen in FIGS. 8*d*-8*f*, wall portion 230 should be flexible and of a thickness so as to invert as compared to FIGS. 8*a*-8*c*, while wall portion 232 should be more rigid so that it does not invert, however, the opposite could also be true in other various embodiments. This is accomplished by making wall portion 230 thinner than wall portion 232, but that is not necessarily true as other factors, such as materials, could be used to attain the same effect. The thickness of the wall portions 230 and 232 should not matter with respect to its respective members 210*a* and 210*b*, other than that wall portions 230 should deform much more than compared to the rest of member 210*a*. The thickness of the wall portions 230 and 232 in FIGS. 8*a*-8*f* are similar, however, they are not required to be similar, and may vary in thickness with relation to each other as required by various processes that could cause wall portion 230 in FIGS. 8*a*-8*c* to invert to the form in FIGS. 8*d*-8*f*.

As shown in the progression between FIGS. 8*a* and 8*b*, the chamber 212 is at least partially filled with the first desired sample fluid 250 from a reservoir such as reservoir 214 in FIG. 6. The fluids in the various embodiments are transferred to chambers through the various channels via a known method of filling, such as vacuum or centrifugal filling. It should be understood that this method of filling and the order of filling may be varied and is only given as an exemplary method of filling. Once the chamber 212 is at least partially filled, the channels 262 of channel network 216 leading to the chambers 212 through channel portions 262*a* are staked or otherwise sealed off as shown in FIG. 8*c*. For channels 262 and 262*a*, a staked portion 258 of the channel surface portion 236 of the inner surface 217 of member 210*a* would come into contact with a staked portion 256 of the channel surface portion 235 of the top surface 220*a* of wall 220. Additional methods of staking have been described earlier in the specification.

In FIGS. 8*a*-8*f*, once the channels 262 have been staked, the wall portion 230 is inverted from being concave as in FIGS. 8*a*-8*c* to being convex as in FIGS. 8*d*-8*f*. In this embodiment and other various embodiments, this inverting the wall portion 230 through a pop or snap action can be accomplished in several ways, only one of which is disclosed here. Other methods of pop or snap action are described in, for example, pending U.S. patent application Ser. No. 10/309,311 filed on Dec. 4, 2002, commonly assigned, the complete disclosure of which is hereby incorporated by reference for any purpose. One exemplary method is that a vacuum could be applied to at least the domed chamber surface portion 226 of outer surface 213 of wall portion 230 that would create suction and cause wall portion 230 to invert. Another exemplary method would be to apply a heating element to at least the domed chamber surface portion 226 of outer surface 213 of wall portion 230 so that the heat would cause the wall portion 230 to deform and cause wall portion 230 to invert. The steps of applying a force to a sample chamber portion, heating a sample chamber portion, and applying a vacuum to a sample chamber portion, are each individually also referred to as "initiating" at least one of the sample chamber portions so that the first and second fluids are in fluid communication with each other. While wall portion 230 inverts, however, as seen in FIGS. 8*a*-8*f*, bottom wall portion 232 remains the substantially the same, ideally with no change in shape or structure to the wall portion 232, but a small change in shape or size due to external forces is contemplated and acceptable. Thus, as shown in FIGS. 8*d*-8*f*, the sample chamber 212 is now greater in size, indeed it has expanded, as compared to the sample chamber shown in FIGS. 8*a*-8*c*. The step of expanding the sample chamber is also referred to as "initiating" at least one of the sample chamber portions so that the first and second fluids are in fluid communication with each other. Once wall portion 230 has been inverted, the chamber 212 is filled with the second desired sample fluid 252 from a reservoir such as reservoir 214X in FIG. 6. The fluids in the various embodiments are transferred to chambers through the various channels via a known method of filling, such as vacuum or centrifugal filling, or passive or active transport as known in the art of microfluidics. It should be understood that this method of filling and the order of filling may be varied and is only given as an exemplary method of filling. When the sample fluid 252 enters chamber 212, it simultaneously mixes with sample fluid 250 already in the chamber 212 and thus forms composition 254. Once the chamber 212 is at least partially but possibly completely filled with composition 254, the channels 260 of channel network 216 leading to the chambers 212 through channel portions 260*a* are staked or otherwise sealed off as shown in FIG. 8*f*. For channels 260 and 260*a*, a staked portion 257 of the channel surface portion 234 of the inner surface 222 of member 210*b* would come into contact with a staked portion 255 of the channel surface portion 233 of the bottom surface 220*b* of wall 220. Additional methods of staking have been described earlier in the specification. The microcard with its plurality of chambers is now ready to be further processed.

It will be apparent to those skilled in the art that various modifications and variations can be made to the structure and methods described above. Thus, it should be understood that the present teachings are not limited to the examples discussed in the specification. Rather, the present teachings are intended to cover modifications and variations.

What is claimed is:

1. A sample substrate for biological samples, comprising:

a first chamber portion configured to contain a biological sample at least partially defined by a first member;

a second chamber portion configured to contain a biological sample at least partially defined by a second member; and a wall positioned between the first and second chamber portions, wherein in the first position the first member is convex, the second member is concave, and the wall is continuous and prevents fluid communication between the first and second chamber portions, and in a subsequent second position the first member is concave, the second member is convex, and the wall is discontinuous and permits fluid communication between the first and second chamber portions.

2. The sample substrate of claim 1, wherein the first member, the second member, and the wall are each made out of one of polypropylene, polycarbonate thermoplastic, and biaxially-oriented polyethylene terephthalate.

3. The sample substrate of claim 1, wherein the first chamber portion, the second chamber portion, and the wall further comprise a hydrophilic coating covering at least a portion respectively thereof.

4. The sample substrate of claim 1, further comprising a projection positioned in the first chamber portion, the projection configured to breach the wall.

5. The sample substrate of claim 4, wherein the projection comprises at least one pointed projection.

6. The sample substrate of claim 4, wherein the projection is integrally attached to the first chamber portion.

* * * * *